US00PP26994P3

(12) United States Plant Patent
Wood

(10) Patent No.: US PP26,994 P3
(45) Date of Patent: Aug. 2, 2016

(54) *SPIRAEA* PLANT NAMED 'SMSJDG03'

(50) Latin Name: *Spiraea japonica*
Varietal Denomination: SMSJDG603

(71) Applicant: Timothy Wood, Spring Lake, MI (US)

(72) Inventor: Timothy Wood, Spring Lake, MI (US)

(73) Assignee: Spring Meadows Nursery, Inc., Grand Haven, MI (US)

( * ) Notice: Subject to any disclaimer, the term of this patent is extended or adjusted under 35 U.S.C. 154(b) by 16 days.

(21) Appl. No.: 14/544,344

(22) Filed: Dec. 23, 2014

(65) Prior Publication Data

US 2016/0183427 P1 Jun. 23, 2016

(51) Int. Cl.
*A01H 5/00* (2006.01)

(52) U.S. Cl.
USPC ..... Plt./226

(58) Field of Classification Search
USPC ..... Plt./226
CPC ..... A01H 5/0216; A01H 5/02
See application file for complete search history.

*Primary Examiner* — Kent L Bell
(74) *Attorney, Agent, or Firm* — Cassandra Bright

(57) ABSTRACT

A new and distinct *Spiraea* cultivar named 'SMSJDG603' is disclosed, characterized by Attractive, gold foliage complimented with unique red colored new growth. Plants are compact, low and mounded, performing well in commercial contianers. Flowers are bright pink and foliage resists sunburn. The new variety is a *Spiraea*, normally produced as an outdoor garden or container plant.

2 Drawing Sheets

Latin name of the genus and species: *Spiraea japonica.*
Variety denomination: 'SMSJDG603'.

BACKGROUND OF THE INVENTION

The new *Spiraea* cultivar is the product of a planned breeding program conducted by the inventor, Timothy D. Wood, in Grand Haven, Mich. The objective of the breeding program was to produce new *Spiraea* varieties of compact and full habit with novel and improved flower and leaf colors. The open pollination resulting in this new variety was made during June of 2004.

The seed parent is the commercial variety, *Spiraea japonica* 'Walbama' U.S. Plant Pat. No. 9,363. The pollen parent is unknown as it was an open pollination breeding program. The new variety was identified as a potentially interesting selection in June of 2006, at a nursery in Grand Haven, Mich.

Asexual reproduction of the new cultivar 'SMSJDG603' by softwood cuttings was first performed during June of 2006, at commercial greenhouse in Grand Haven, Mich. Subsequent propagation has shown that the unique features of this cultivar are stable and reproduced true to type in 6 successive generations.

SUMMARY OF THE INVENTION

The cultivar 'SMSJDG603' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'SMSJDG603' These characteristics in combination distinguish 'SMSJDG603' as a new and distinct *Spiraea* cultivar:

1. Attractive, gold foliage complimented with unique red colored new growth.
2. Compact low mounded habit.
3. Attractive narrow foliage.
4. Bright pink flowers.
5. Foliage looks good all summer, resisting sunburn.
6. Good performance in commercial container production.

PARENT COMPARISON

Plants of the new cultivar 'SMSJDG603' are similar to plants of the seed parent, the commercial variety, *Spiraea japonica* 'Walbama' U.S. Plant Pat. No. 9,363 in most horticultural characteristics, however, plants of the new cultivar 'SMSJDG603' differ in the following:

1. Narrower leaves.
2. Lower growth habit.

COMMERCIAL COMPARISON

Plants of the new cultivar 'SMSJDG603' can also be compared to the commercial variety *Spiraea* 'Yan', U.S. Plant Pat. No. 21,615. These varieties are similar in most horticultural characteristics; however 'SMSJDG603' differs in the following:

1. Foliage with red new growth
2. Narrower leaves

BRIEF DESCRIPTION OF THE PHOTOGRAPHS

Figure 1:
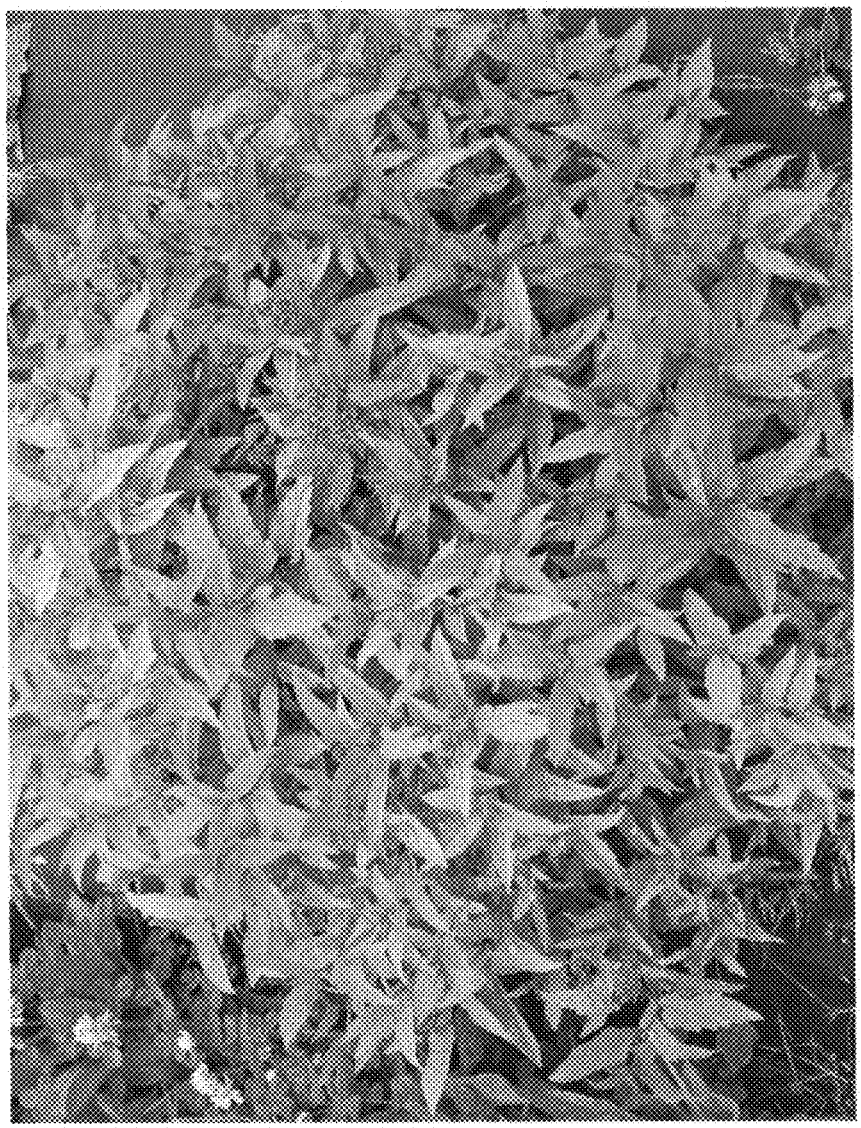

The accompanying photograph in FIG. 1 illustrates in full color a typical plant of 'SMSJDG603', with unique red new growth.

Figure 2:
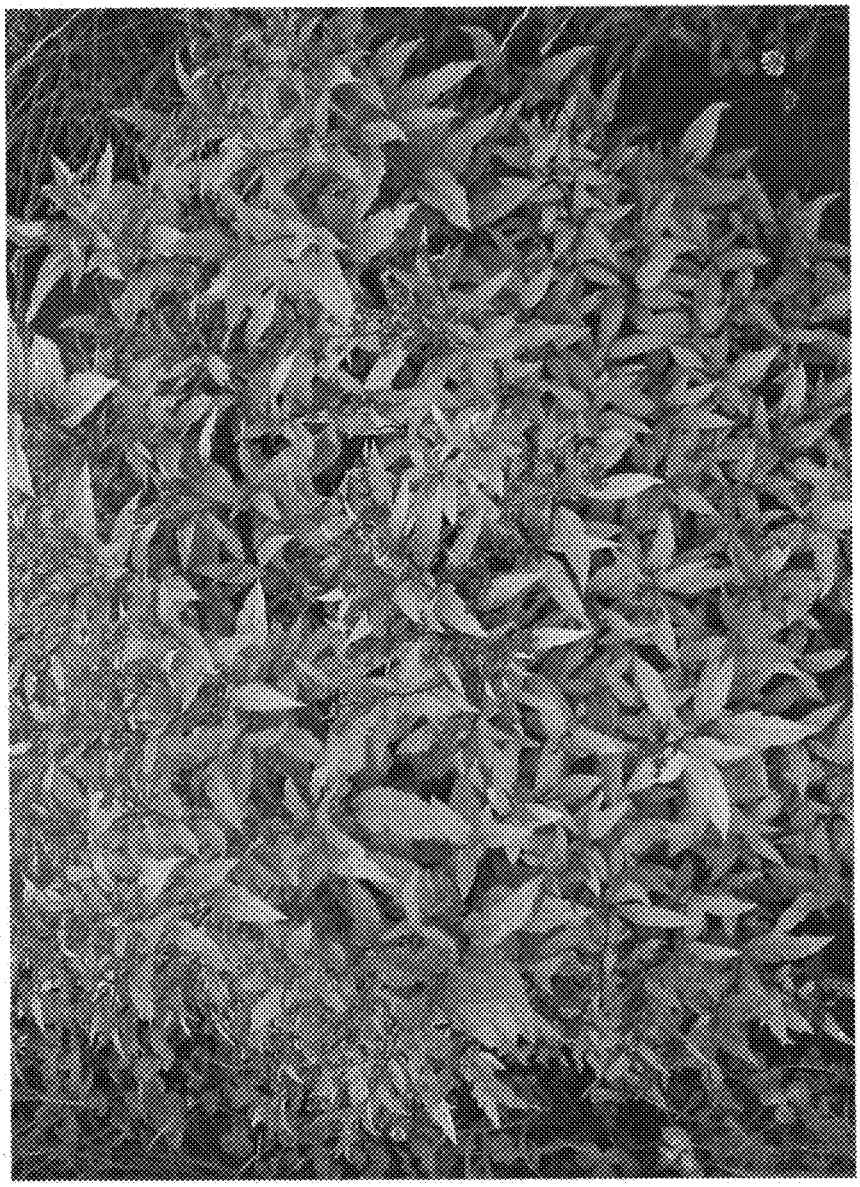

FIG. 2 illustrates in full color a typical plant of 'SMSJDG603' grown outdoors, in Grand Haven, Mich., in a commercial 2 gallon container. Age of the plant photographed is approximately 2 years.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 1995 except where general terms of ordinary dictionary significance are used. The following observations and measurements describe 'SMSJDG603' plants grown in a commercial greenhouse in Grand Haven, Mich. Description was made during Mid July of 2014. The plants were 2 to 3 years old grown in 2 gallon containers. The growing temperature ranged from 10° C. to 38° C. Measurements and numerical values represent averages of typical plant types.

Botanical classification: *Spiraea japonica* 'SMSJDG603'.

PROPAGATION

Time to initiate roots: About 15 days at approximately 22° C.

Root description: Fibrous, moderate to dense density medium thickness and freely branching. Cream to brown in color, not effectively measured with a color chart.

Time to produce a rooted young plant: About 2 months at 22° C.

PLANT

Plant type: Perennial shrub.

Age of plant described: Approximately 2 to 3 years old.

Growth habit: Compact low and mounded.

Pot size of plant described: 2 gallon pot.

Height: Approximately 20 to 36 cm to top of foliage.

Plant spread: Approximately 15 to 20 cm.

Growth rate: Moderate.

Plant vigor: Strong.

Branching characteristics: Strong branching, some basal branching, some pinching required.

Length of primary lateral branches: Average 16.8 cm.

Diameter of lateral branches: Approximately 1.5 to 2.5 cm.

Quantity of lateral branches: About 30.

Stem:

- *Stem appearance*.—Round.
- *Stem strength*.—Sturdy.
- *Stem color*.—New: Near RHS Yellow-Green 145A. Old: Near RHS Greyed-Orange 175A. Meristem: Near RHS Greyed-Orange 177A.
- *Pubescence*.—Very slight.
- *Aspect*.—Straight and upright.
- *Other stem characteristics*.—Older woody bark slightly exfoliated.

Internode length: Average 1.0 to 2.5 cm.

FOLIAGE

Leaf:

- *Arrangement*.—Alternate/Sub-alternate, compound.
- *Leaf shape*.—Lanceolate.
- *Quantity*.—Approximately 12 fully expanded per main branch.
- *Average length*.—Approximately 4.5 cm.
- *Average width*.—Approximately 2.5 cm.
- *Shape of blade*.—Ovate-oblanceolate.
- *Apex*.—Acute.
- *Base*.—Cuneate.
- *Margin*.—Serrulate.
- *Texture of top surface*.—Slightly pubescent with vein indentation.
- *Texture of bottom surface*.—Slightly smooth with small and large raised veins causing ridges.
- *Color*.—Young foliage upper side: Varies between Near RHS Yellow-green 152A, 152B and 152C with tinges of Greyed-Orange 172A and 172B. This combination gives the overall appearance of a red flush. Young foliage under side: Near RHS Yellow-Green 146C with tinges of Greyed-Orange 172B. This combination gives the overall appearance of a red flush. Mature foliage upper side: Near RHS Yellow-Green 146B. Mature foliage under side: Near RHS Green 138B.
- *Venation*.—Color upper side: New Growth: Near RHS Yellow-Green 145C. Old Growth: Near RHS Green 145C. Color under side: New Growth: Near RHS Yellow-Green 145A. Old Growth: Near RHS Yellow-Green 145A.
- *Petiole*.—Average Length: Approximately 2 to 5 mm. Diameter: 0.5 to 1.0 mm. Petiole color upper side: New growth: Near RHS Greyed-Orange 174C with touches of Yellow-Green 144B. Old growth: Near RHS Yellow-Green 144B. Petiole color lower side: New growth: Near RHS Greyed-Orange 174C with touches of Yellow-Green 144B. Old growth: Near RHS Yellow-Green 145A. Petiole Texture upper side: Smooth. Petiole Texture lower side: Smooth.
- *Other foliage characteristics*.—Stipules at base of petiole, 1.5 to 2.0 mm, near RHS Red-Purple 66A.

FLOWER

Natural flowering season: Spring through Summer.

Flower arrangement: Single rotate flowers on terminal corymbs.

Inflorescence type and habit: Corymb.

Flower longevity on plant: 3 to 4 weeks.

Quantity of flowers per inflorescence: About 40-100.

Inflorescence size:

- *Width*.—Approximately 30-50 mm.
- *Height*.—Approximately 25-40 mm.

Quantity of flowers per lateral stem: 100-500.

Quantity of flower buds per lateral stem: 50-100.

Quantity of flowers per plant: Average of 6,175.

Individual flowers:

- *Flower form*.—Single, rotate.
- *Flower aspect*.—Upright and outward.
- *Flowering habit*.—Terminal.
- *Size*.—Diameter: Approximately 7 mm. Length: Approximately 5 mm. Depth: Approximately 4 mm.
- *Flower other characteristics*.—Persistence: Self cleaning. Fragrance: Very faint, sweet.

Petal:

- *Petal arrangement*.—Single whorl of five of six petals.
- *Number of petals per flower*.—5-6.
- *Petal shape*.—Ovate.
- *Petal base*.—Obtuse/Truncate.
- *Margin*.—Slightly undulate.
- *Tip shape*.—Acute.
- *Length*.—3-4 mm.
- *Width*.—2-3 mm.
- *Texture*.—Upper: Smooth. Lower: Smooth.

Petal color:

*When opening*.—Upper surface: Near RHS Red-Purple 63A. Lower surface: Soft fade near RHS Red-Purple 63B.

*Fully opened*.—Upper surface: Near RHS Red-Purple 63B. Lower surface: Near RHS Red-Purple 63D.

Bud:

*Shape*.—Globose.

*Length*.—Approximately 1.5-2.5 mm.

*Diameter*.—Approximately 1.0-1.5 mm.

*Color*.—Near RHS Red-Purple 59B.

Sepals:

*Shape*.—Ovate.

*Arrangement*.—Single whorl of 5 sepals.

*Number of sepal*.—5.

*Length*.—Approximately 1.5 mm.

*Width*.—Approximately 1 mm.

*Margin*.—Entire.

*Base*.—Fused.

*Tip*.—Acute to Acuminate.

*Texture*.—Fairly smooth.

*Color*.—Upper side: Near RHS Greyed-green 198A. Lower side: Near RHS Greyed-green 191B.

Peduncle:

*Length*.—20-35 mm.

*Diameter*.—1 mm.

*Color*.—Near RHS Yellow-green 148A.

*Orientation*.—Upright and outward.

*Strength*.—Fairly strong, flexible.

*Texture*.—Smooth.

Pedicel:

*Length*.—3-5 mm.

*Diameter*.—0.5 mm.

*Color*.—Near RHS Yellow-green 148A.

*Orientation*.—Upright and outward.

*Strength*.—Fairly strong.

*Texture*.—Fairly smooth.

REPRODUCTIVE ORGANS

Stamens:

*Number*.—25-30.

*Filament length*.—2.5-3.5 mm.

*Filament color*.—Near RHS Red 52B.

Anthers:

*Shape*.—Globose.

*Length*.—Approximately 0.33 mm.

*Color*.—Near RHS Black 202A.

*Pollen color*.—Between RHS White 155B and 155C.

Pistil:

*Number*.—4.

*Length*.—Approximately 2 mm.

*Style*.—Length: Approximately 2 mm. Color: Near RHS Red 51A.

*Stigma*.—Shape: Oblong. Color: Near RHS Black 202A. Ovary color: Near RHS Red 56B.

OTHER CHARACTERISTICS

Seeds and fruits: Not observed to date.

Garden performance: Excellent performance in a garden setting.

Disease/pest resistance: Good mildew resistance observed. Neither resistance nor susceptibility to normal diseases and pests of *Spiraea* have been observed.

Temperature tolerance: The new variety tolerates temperatures between −31° C. to 38° C.

What is claimed is:

1. A new and distinct cultivar of *Spiraea* plant named 'SMSJDG603' as herein illustrated and described.

* * * * *